United States Patent

Krämer et al.

[11] 4,145,428
[45] Mar. 20, 1979

[54] FUNGICIDALLY ACTIVE 2-ACYLOXY-1-PHENOXY-1-(1,2,4-TRIAZOLYL)-3,3-DIMETHYL-BUTANES

[75] Inventors: Wolfgang Krämer; Karl H. Büchel, both of Wuppertal; Wilhelm Brandes, Cologne; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 753,651

[22] Filed: Dec. 21, 1976

[30] Foreign Application Priority Data

Jan. 10, 1976 [DE] Fed. Rep. of Germany ....... 2600799

[51] Int. Cl.² ...................... A01N 9/22; A61K 31/41; C07D249/10
[52] U.S. Cl. .................................. 424/269; 260/299; 260/308 R; 424/245
[58] Field of Search .......................... 260/308 R, 299; 424/269, 245

[56] References Cited

U.S. PATENT DOCUMENTS 3,952,002   4/1976   Kramer et al. .................. 260/308 R

FOREIGN PATENT DOCUMENTS 500663   2/1971   Switzerland ......................... 260/479 R

OTHER PUBLICATIONS

Berger, Medicinal Chemistry (Second Edition, New York, 1960), pp. 1051-1053.

*Primary Examiner*—Alton D. Rollins
*Attorney, Agent, or Firm*—Sprung, Felfe, Horn, Lynch & Kramer

[57] ABSTRACT

1-Phenoxy-1-(1,2,4-triazolyl)-3,3-dimethyl-butanes of the formula

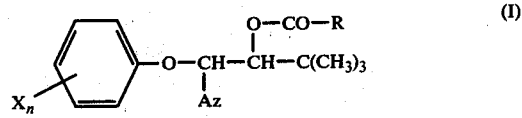

in which
R represents alkyl, alkenyl, alkynyl, cycloalkyl, halogenoalkyl, optionally substituted phenyl, optionally substituted phenoxyalkyl, alkylamino, dialkylamino or optionally substituted phenylamino,
X represents halogen, alkyl, cycloalkyl, alkoxy, halogenoalkyl, alkylthio, alkoxycarbonyl, optionally substituted phenyl, optionally substituted phenoxy, optionally substituted phenylalkyl, amino, cyano or nitro,
n represents 0, 1, 2, 3, 4 or 5, and
Az represents the 1,2,4-triazolyl-1 or the 1,2,4-triazolyl-4 radical, in the form of the free base, a salt with a physiologically tolerated acid or a complex with a metal salt, which possess fungicidal properties.

9 Claims, No Drawings

FUNGICIDALLY ACTIVE 2-ACYLOXY-1-PHENOXY-1-(1,2,4-TRIAZOLYL)-3,3-DIMETHYL-BUTANES

The present invention relates to and has for its objects the provision of particular new 1-phenoxy-1-(1,2,4-triazolyl)-3,3-dimethyl-butanes which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has been disclosed in U.S. Pat. No. 3,952,002 that triazolyl-O,N-acetals, especially 1-phenoxy-1-[1,2,4-triazolyl-(1)]-3,3-dimethylbutan-2-ols which are substituted in the phenyl part, possess good fungicidal properties. However, their activity is not always entirely satisfactory, especially when low amounts and low concentrations are used. Furthermore, their toleration by plants, and their toleration by seed when used as a seed dressing, is not always satisfactory.

The present invention now provides, as new compounds, the acylated triazolyl-O,N-acetals of the general formula

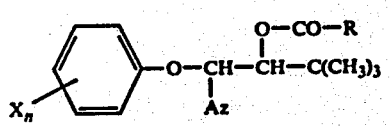     (I)

in which
R represents alkyl, alkenyl, alkynyl, cycloalkyl, halogenoalkyl, optionally substituted phenyl, optionally substituted phenoxyalkyl, alkylamino, dialkylamino or optionally substituted phenylamino,
X represents halogen, alkyl, cycloalkyl, alkoxy, halogenoalkyl, alkylthio, alkoxycarbonyl, optionally substituted phenyl, optionally substituted phenoxy, optionally substituted phenylalkyl, amino, cyano or nitro,
n represents 0, 1, 2, 3, 4 or 5, and
Az represents the 1,2,4-triazolyl-1 or the 1,2,4-triazolyl-4 radical,
in the form of the free base, a salt with a physiologically tolerated acid or a complex with a metal salt.

Preferably, R represents straight-chain or branched alkyl with 1 to 8 (especially 1 to 6) carbon atoms, straight-chain or branched alkenyl or alkynyl, each with 2 to 4 carbon atoms, halogenoalkyl with 1 or 2 carbon atoms and 1 to 5 halogen atoms (especially fluorine and chlorine), cycloalkyl with 5 to 7 carbon atoms (especially cyclohexyl), or optionally substituted phenyl or phenoxyalkyl which is optionally substituted in the phenyl part and has up to 2 carbon atoms in the alkyl part, in either case the substituents being selected from halogens, amino, cyano, nitro and alkyl with 1 or 2 carbon atoms, or R represents alkylamino or dialkylamino with 1 to 4 (especially 1 or 2) carbon atoms in the or each alkyl part, or phenylamino which may optionally be substituted by halogen, nitro or cyano; X represents halogen, amino, cyano, nitro, straight-chain or branched alkyl with up to 4 carbon atoms, cycloalkyl with 5 to 7 carbon atoms (especially cyclohexyl), halogenoalkyl with up to 2 carbon atoms and up to 5 halogen atoms (especially fluorine atoms and chlorine atoms), alkoxycarbonyl with a total of up to 5 carbon atoms, alkoxy or alkylthio each with up to 2 carbon atoms, phenyl or phenoxy, either of which may optionally carry one or more substituents selected from halogens, amino, cyano, nitro and alkyl with 1 to 2 carbon atoms, or phenylalkyl with 1 or 2 carbon atoms in the alkyl part, in which alkylcarbonyloxy with a total of up to 3 carbon atoms may be a substituent in the alkyl part and halogen, nitro or cyano may be a substituent in the phenyl part; and n represents 0, 1, 2 or 3.

The compounds of the formula (I) possess two asymmetrical carbon atoms; they can therefore exist in the erythro-form and in the threo-form. In both cases they are predominantly in the form of racemates.

Surprisingly, the acylated triazolyl-O,N-acetals according to the invention exhibit a substantially greater fungicidal activity, especially against species of rust and mildew, than the triazolyl-O,N-acetals known from the state of the art, which are the most closely related active compounds. Furthermore, they are distinguished by better toleration by plants. The active compounds according to the invention thus represent an enrichment of the art.

The present invention also provides a process for the preparation of an acylated triazolyl-O,N-acetal of the formula (I), in which a triazolyl derivative of the general formula

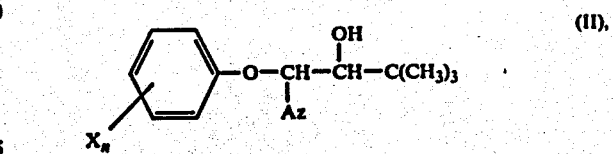     (II), in which X, Az and n have the above-mentioned meanings,
(a) is reacted with an acid halide of the general formula

     (III), in which
R has the above-mentioned meaning and
Hal represents halogen, especially chlorine or bromine,
in the presence of a solvent, and the hydrohalide so formed is converted into the free base, if required, or
(b) is reacted with an acid anhydride of the general formula

     (IV), in which R has the above-mentioned meaning,
in the presence of a solvent and optionally in the presence of a catalyst, or
(c) is reacted with a ketene of the general formula

     (V), in which R' represents hydrogen, alkyl, alkenyl, alkynyl or halogenomethyl,
in the presence of a solvent and optionally in the presence of a catalyst, or
(d) is reacted with an isocyanate of the general formula

     (VI), which R" represents alkyl or optionally substituted phenyl,
the presence of a solvent and optionally in the presence of a catalyst, and, if required, the acylated triazo--O,N-acetal obtained in any of the process variants -(d) is converted into a physiologically tolerated salt metal complex thereof.

The acylated triazolyl-O,N-acetals of the formula (I) can be converted into their salts by reaction with acids, into their metal complexes by reaction with metal salts.

If 1-(4-chlorophenoxy)-1-[1,2,4-triazolyl-(1)]-3,3-methyl-butan-2-ol and acetyl chloride are used as starting materials in process variant (a), the course of the reaction can be represented by the following equation:

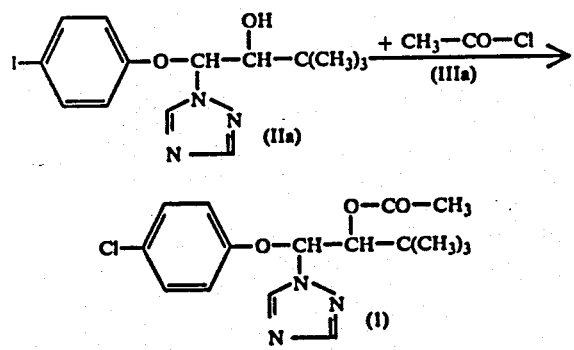

If 1-(4-chlorophenoxy)-1-[1,2,4-triazolyl-(1)]-3,3-methyl-butan-2-ol and acetic anhydride are used as starting materials in process variant (b), the course of the reaction can be represented by the following equation:

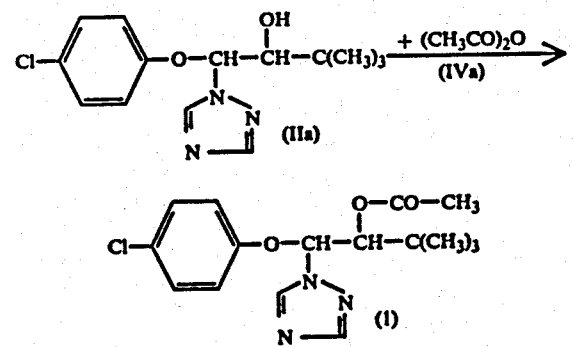

If 1-(2,4-dichlorophenoxy)-1-[1,2,4-triazoly-(1)]-3,3-dimthyl-butan-2-ol and 4-chlorophenylisocyanate are used as starting materials in process variant (d), the course of the reaction can be represented by the following equation:

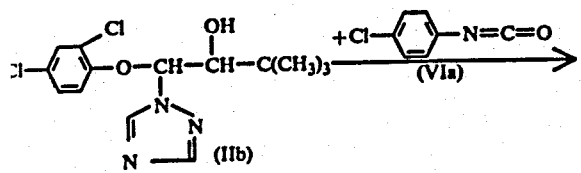

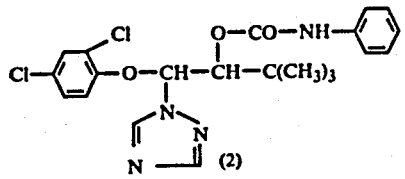

Reactions of triazolyl derivatives of the formula (II) with a ketene of the formula (V), according to process variant (c), can be formulated analogously.

The starting materials of the formula (II) are generally known from U.S. Pat. No. 3,952,002 and can be obtained in accordance with the processes already described, by, for example, reducing the corresponding ketone derivatives with aluminum isopropylate or with complex hydrides in the presence of a solvent.

The acid halides of the formula (III) are known be prepared in accordance with customary processes such as, for example, by reaction of carboxylic acids or their alkali metal salts with acid halides of phosphorus or sulfur. These methods are known from the general textbooks of organic chemistry.

The acid anhydrides of the formula (IV) are known and can be prepared in accordance with known processes such as, for example, by the action of acid chlorides on the alkali metal salts of the carboxylic acids. These processes are generally known.

The formula (V) provides a general definition of the ketenes required as starting materials in process variant (c). Here, R' preferably represents hydrogen, alkyl with 1 to 7, especially 1 to 5, carbon atoms, alkenyl or alkynyl each with up to 3 carbon atoms, or halogenomethyl with 1 to 3 halogen atoms, especially fluorine and chlorine. The ketenes which can be used for the reaction are also known and can be prepared in accordance with known processes such as, for example, by thermolysis of ketones or by dehydration of carboxylic acids (see Houben-Weyl, "Methoden der organischen Chemie" ("Methods of Organic Chemistry") volume 7/4, Georg Thieme Verlag).

The formula (VI) provides a general definition of the isocyanates required as starting materials in process variant (d). In this formula, R" preferably represents alkyl with 1 to 4, especially 1 or 2, carbon atoms, or optionally substituted phenyl, with halogen, nitro and cyano being the preferred substituents.

Possible salts of the compounds of the formula (I) are salts with physiologically tolerated acids, especially the hydrogen halide acids such as hydrobromic acid and, especially, hydrochloric acid; phosphoric acid; nitric acid; monofunctional and bifunctional carboxylic acids and hydroxycarboxylic acids, such as, for example, acetic acid, maleic acid, succinic acid, fumaric acid, tartaric acid, citric acid, salicyclic acid, sorbic acid and lactic acid; and 1,5-naphthalene-disulfonic acid.

The salts of the compounds of the formula (I) can be obtained in a simple manner in accordance with customary methods of forming salts, for example by dissolving the base in ether, for example diethyl ether, and adding the acid, for example nitric acid, and can be isolated in a known manner, for example by filtering off, and be purified if required.

Possible complexes of the compounds of the formula (I) are complexes with metal salts. In this context, metals of main groups (II) to (IV) and of sub-groups (I), (II) and (IV) to (VIII) should be mentioned, especially copper, zinc, manganese, magnesium, tin, iron and nickel. These metals are used as salts with physiologically tolerated acids, especially the hydrogen halide acids, such as hydrochloric acid and hydrobromic acid, as well as phosphoric acid, nitric acid and sulfuric acid.

The metal complexes of the compounds of the formula (I) can be obtained in a simple manner in accordance with customary processes, such as, for example, by dissolving the metal salt in alcohol, for example ethanol, and adding it to the base. The complexes can be isolated in a known manner, for example by filtering off, and can, if required, be purified by recrystallization.

Preferred solvents for the reaction according to process variant (a) are inert organic solvents, especially ketones, such as diethyl ketone and, especially, acetone and methyl ethyl ketone; nitriles, such as propionitrile and, especially, acetonitrile; ethers, such as tetrahydrofuran or dioxane; esters, such as ethyl acetate; aromatic hydrocarbons, such as benzene or toluene; and halogenated hydrocarbons, such as methylene chloride, carbon tetrachloride or chloroform.

In carrying out process variant (a) the reaction temperatures can be varied within a fairly wide range. In general, the reaction is carried out at between 0° and 100° C., preferably between 20° and 85° C. If a solvent is present, the reaction is advantageously carried out at the boiling point of the particular solvent.

In carrying out process variant (a), equimolar quantities of the starting materials are preferably used. The compounds of the formula (I) are obtained in the form of their hydrohalides and can be isolated as such, by precipitating them by adding the organic solvent, for example hexane, filtering them off and, if required, purifying them by recrystallization. The compounds of the formula (I) can also be isolated in the form of the free base, by adding aqueous sodium bicarbonate solution to the reaction mixture and isolating the base in accordance with customary methods.

Preferred diluents for the reaction according to process variant (b) are inert organic solvents, especially the solvents listed in connection with process variant (a); however, the acid anhydride of the formula (IV) used in each particular case may also be employed as the solvent.

Preferred catalysts which can be used in process variant (b) are customary acid and basic catalysts such as, for example, sulfuric acid, hydrogen chloride, hydrogen bromide, boron trifluoride, zinc chloride, sodium acetate, sodium benzoate, sodium carbonate, calcium oxide and magnesium oxide.

In carrying out process variant (b), the reaction temperatures can be varied within a fairly wide range. In general, the reaction is carried out at between 0° and 150° C. and preferably between 80° and 120° C.

In carrying out process variant (b), equimolar quantities of the reactants are preferably used. However, for simplicity, the acid anhydride of the formula (IV) can also be used as the solvent, in which case an appropriate excess becomes necessary. The compounds of the formula (I) may be isolated in the usual manner.

Preferred diluents which can be used for the reaction according to process variant (c) are inert organic solvents, especially the solvents listed in connection with process variant (a).

In carrying out process variant (c), the reaction temperatures can be varied within a fairly wide range. In general, the reaction is carried out at between −10° and 70° C. and preferably between 0° and 40° C.

Preferred diluents which can be used for the reaction according to process variant (d) are inert organic solvents, especially the solvents listed in connection with process variant (a).

Catalysts which can be used preferably in process variant (d) are tertiary bases, such as triethylamine and pyridine, or organo-tin compounds, such as dibutyl-tin dilaurate.

In carrying out process variant (d), the reaction temperatures can be varied within a fairly wide range. In general, the reaction is carried out at between 0° and 100° C. and preferably between 20° and 40° C.

In carrying out process variant (d), equimolar quantities of the reactants are preferably used. To isolate the compounds of the formula (I), the solvent is distilled off and the residue is worked up in accordance with customary methods.

The active compounds according to the invention exhibit a powerful fungitoxic and bacteriotoxic action. They do not damage crop plants in the concentrations required to combat fungi and bacteria. For these reasons, they are suitable for use as plant protection agents for combating fungi and bacteria. Fungitoxic agents are employed in plant protection for combating Plasmodiophoromycetes, Oomycetes, Chytridiomycetes, Zygromycetes, Ascomycetes, Basidiomycetes and Deuteromycetes.

The active compounds according to the invention have a broad spectrum of action and can be used against parasitic fungi which attack above-ground parts of plants or attack the plants through the soil, and also against seed-borne pathogens.

The active compounds display a particularly good activity against parasitic fungi on above-ground parts of plants, such as species of Erysiphe and species of Venturia, and also against species of Pyricularia and species of Pellicularia. Good effects are achieved against the pathogens of bean rust (*Uromyces phaseoli*), of late blight (*Phytophthora infestans*), and against fungi which cause powdery mildew diseases, such as, for example, the pathogen of powdery mildew of cereals (*Erysiphe graminis*) and of powdery mildew of apple (*Podosphaera leucotricha*). It is to be emphasized that the active compounds according to the invention not only display a protective action but also are curatively active, that is when used after infection has taken place. Furthermore, the systemic action of the compounds should be pointed out. Thus, it proves possible to protect plants against fungal attack if the active compound is supplied to the above-ground parts of the plant through the soil and the root or through the seed.

As plant protection agents, the compounds according to the invention can be used for the treatment of soil, for the treatment of seed and for the treatment of above-ground parts of plants.

The compounds according to the invention are well tolerated by plants. They have only a low toxicity to warm-blooded animals and, because of their low odour and their good toleration by human skin, they are not unpleasant to handle.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides or insecticides, acaricides, nematicides, bactericides, rodenticides, herbicides, fertilizers, growth-regulating agents, bird repellents, plant nutrients, agents for improving soil structure, etc. if desired or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Especially when used as leaf fungicides, the active compound concentrations in the use forms can be varied within a wide range. In general, they are between 0.1 and 0.00001 percent by weight, and preferably between 0.05 and 0.0001 percent.

For the treatment of seed, amounts of active compound of 0.001 to 50 g per kilogram of seed, preferably 0.01 to 10 g, are generally used.

For the treatment of soil, amounts of active compound of 1 to 1,000 g per cubic meter of soil, preferably of 10 to 200 g, are generally used.

Furthermore, the present invention contemplates methods of selectively killing, combating or controlling pests, e.g. fungi, which comprises applying to at least one of correspondingly (a) such fungi, and (b) the corresponding habitat thereof, i.e. the locus to be protected, e.g. to a growing crop, to an area where a crop is to be grown or to a domestic animal, a correspondingly combative or toxic amount, i.e. a fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Uromyces test (bean rust)/protective

Solvent: 4.7 parts by weight of acetone
Emulsifier: 0.3 part by weight of alkylaryl polyglycol ether
Water: 95 parts by weight The amount of active compound required for the desired concentration of active compound in the spray liquor was mixed with the stated amount of the solvent and the concentrate was diluted with the stated amount of water which contained the stated additives.

The young bean plants, which were in the 2-leaved stage, were sprayed with the spray liquor until dripping wet. The plants remained in a greenhouse for 24 hours at 20°–22° C. and a relative atmospheric humidity of 70% in order to dry. They were then inoculated with an aqueous uredospore suspension of the causative organism of bean rust (*Uromyces phaseoli*) and incubated for 24 hours in a dark humidity chamber at 20°–22° C. and 100% relative atmospheric humidity.

The plants were then set up in a greenhouse under intensive illumination for 9 days at 20°–22° C. and a relative atmospheric humidity of 70–80%.

10 days after the inoculation, the infection of the plants was determined. The ratings were converted to percent infection. 0% denoted no infection and 100% denoted that the plants were completely infected.

The active compounds, active compound concentrations and results can be seen from the following table:

Table 1

| Uromyces test/protective | |
|---|---|
| Active compound | Infection in % of the infection of the untreated control at an active compound concentration of 0.005% |
| 4-chloro-2-methylphenyl derivative (known) (A) | 59 |
| 2,4,5-trichlorophenyl derivative (known) (B) | 59 |
| 4-methylphenyl derivative (known) (C) | 54 |
| 2,4-dichlorophenyl O-CO-CH₃ derivative (5) | 46 |
| 4-chlorophenyl O-CO-CH₃ derivative (1) | 22 |
| 2,4-dichlorophenyl O-CO-CH₂-CH(CH₃)₂ derivative (36) | 46 |
| 4-iodophenyl O-CO-CH₃ derivative (29) | 16 |

Table 1-continued

Uromyces test/protective

| Active compound | Infection in % of the infection of the untreated control at an active compound concentration of 0.005% |
|---|---|
| Compound (31): 4-O₂N-C₆H₄-O-CH(N-triazolyl)-CH(O-CO-CH₃)-C(CH₃)₃ | 16 |
| Compound (34): 4-Cl-C₆H₄-C₆H₄-O-CH(N-triazolyl)-CH(O-CO-CH₃)-C(CH₃)₃ | 0 |
| Compound (2): 2,4-Cl₂-C₆H₃-O-CH(N-triazolyl)-CH(O-CO-NH-C₆H₄-4-Cl)-C(CH₃)₃ | 19 |
| Compound (6): C₆H₅-C₆H₄-O-CH(N-triazolyl)-CH(O-CO-CH₃)-C(CH₃)₃ | 0 |
| Compound (9): 2-(C₆H₅)-C₆H₄-O-CH(N-triazolyl)-CH(O-CO-CH₃)-C(CH₃)₃ | 12 |
| Compound (9a): [Cu{2-(C₆H₅)-C₆H₄-O-CH(N-triazolyl)-CH(O-CO-CH₃)-C(CH₃)₃}₂]Cl₂ | 12 |
| Compound (10): C₆H₅-C₆H₄-O-CH(N-triazolyl)-CH(O-CO-(CH₂)₂-CH₃)-C(CH₃)₃ | 9 |
| Compound (19): 2,4,5-Cl₃-C₆H₂-O-CH(N-triazolyl)-CH(O-CO-NH-CH₃)-C(CH₃)₃ | 9 |

EXAMPLE 2

Podosphaera test (apple)/protective

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4- to 6-leaved stage were sprayed with the spray liquid until dripping wet. The plants remained in a greenhouse for 24 hours at 20° C. and at a relative atmospheric humidity of 70%. They were then inoculated by dusting with conidia of the apple powdery mildew causative organism (*Podosphaera leucotricha*) and placed in a greenhouse at a temperature of 21°-23° C. and at a relative atmospheric humidity of about 70%.

10 days after the inoculation, the infection of the seedlings was determined. The ratings were converted to percent infection. 0% meant no infection; 100% meant that the plants were completely infected.

The active compounds, the concentrations of the active compounds and the results can be seen from the following table:

Table 2

Podosphaera test (apple)/protective

| Active compound | Infection in % at an active compound concentration of 0.00031% |
|---|---|
| (CH₃)₃C—C₆H₄—O—CH(triazolyl)—CH(OH)—C(CH₃)₃ (known) (D) | 94 |
| 2-Cl—C₆H₄—O—CH(triazolyl)—CH(OH)—C(CH₃)₃ (known) (E) | 95 |
| 2,4-Cl₂—C₆H₃—O—CH(triazolyl)—CH(O—CO—CH₃)—C(CH₃)₃ (5) | 44 |
| 4-Cl—C₆H₄—O—CH(triazolyl)—CH(O—CO—CH₃)—C(CH₃)₃ (1) | 36 |
| 2,4-Cl₂—C₆H₃—O—CH(triazolyl)—CH(O—CO—NH—C₆H₄—Cl)—C(CH₃)₃ (2) | 27 |
| 2,4-Cl₂—C₆H₃—O—CH(triazolyl)—CH(O—CO—CH₂—CH(CH₃)₂)—C(CH₃)₃ (36) | 57 |

EXAMPLE 3

Shoot treatment test/powdery mildew of cereal/protective (leaf-destructive mycosis)

To produce a suitable preparation of active compound, 0.25 part by weight of active compound was taken up in 25 parts by weight of dimethylformamide and 0.06 part by weight of alkylaryl polyglycol ether emulsifier and then 975 parts by weight of water were added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis var. hordei*.

After 6 days' dwell time of the plants at a temperature of 21°–22° C. and 80–90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The active compound was the more active, the lower was the degree of mildew infection.

The active compounds, active compound concentrations in the spray liquor and degrees of infection can be seen from the table which follows:

Table 3

| Shoot treatment test/powdery mildew of cereal/protective | | | |
|---|---|---|---|
| Active compounds | | Active compound concentration in the spray liquor in % by weight | Infection in % of the untreated control |
| untreated | | — | 100.0 |
| $CH_3$—⬡—O—CH(N-triazole)—CH(OH)—C(CH$_3$)$_3$ (known) | (C) | 0.001 | 60.0 |
| 2-Cl-⬡—O—CH(N-triazole)—CH(OH)—C(CH$_3$)$_3$ (known) | (E) | 0.001 | 82.5 |
| 2,4-Cl$_2$-⬡—O—CH(N-triazole)—CH(O—CO—CH$_3$)—C(CH$_3$)$_3$ | (5) | 0.001 | 0.0 |
| 3-CH$_3$,4-Cl,5-CH$_3$-⬡—O—CH(N-triazole)—CH(O—CO—CH$_3$)—C(CH$_3$)$_3$ | (14) | 0.001 | 3.8 |
| 3,5-(CH$_3$)$_2$-⬡—O—CH(N-triazole)—CH(O—CO—NH—CH$_3$)—C(CH$_3$)$_3$ × HCl | (22) | 0.001 | 50.0 |
| 2-CH$_3$,4-Cl-⬡—O—CH(N-triazole)—CH(O—CO—NH—CH$_3$)—C(CH$_3$)$_3$ | (23) | 0.001 | 50.0 |
| 2-CH$_3$,4-Cl-⬡—O—CH(N-imidazole)—CH(O—CO—NH—CH$_3$)—C(CH$_3$)$_3$ | (44) | 0.001 | 41.3 |

Table 3-continued
Shoot treatment test/powdery mildew of cereal/protective

| Active compounds | | Active compound concentration in the spray liquor in % by weight | Infection in % of the untreated control |
|---|---|---|---|
| 3-Cl, 4-CH$_3$ phenyl-O-CH(triazolyl)-CH(OCONHCH$_3$)-C(CH$_3$)$_3$ × HCl | (24) | 0.001 | 25.0 |
| 4-Cl-phenyl-O-CH(triazolyl)-CH(OCOCH$_3$)-C(CH$_3$)$_3$ | (1) | 0.001 | 0.0 |
| 4-Cl-phenyl-O-CH(triazolyl)-CH(OCOCH$_2$-O-phenyl)-C(CH$_3$)$_3$ | (26) | 0.001 | 55.0 |
| 4-Cl-phenyl-O-CH(triazolyl)-CH(OCOCH$_2$CH$_3$)-C(CH$_3$)$_3$ | (27) | 0.001 | 11.3 |
| 4-Cl-phenyl-O-CH(triazolyl)-CH(OCOCH$_2$Cl)-C(CH$_3$)$_3$ | (28) | 0.001 | 11.3 |
| Cu[3-Cl-phenyl-O-CH(triazolyl)-CH(OCOCH$_3$)-C(CH$_3$)$_3$]$_2$ Cl$_2$ | (4) | 0.001 | 0.0 |
| 4-I-phenyl-O-CH(triazolyl)-CH(OCOCH$_3$)-C(CH$_3$)$_3$ | (29) | 0.001 | 0.0 |
| 2-Cl-phenyl-O-CH(triazolyl)-CH(OCOCH$_3$)-C(CH$_3$)$_3$ | (30) | 0.001 | 33.8 |
| 4-Cl, 2-CH$_3$ phenyl-O-CH(triazolyl)-CH(OCOCH$_3$)-C(CH$_3$)$_3$ | (32) | 0.0005 | 25.0 |
| 3-Cl-biphenyl-O-CH(triazolyl)-CH(OCOCH$_3$)-C(CH$_3$)$_3$ | (33) | 0.0005 | 25.0 |

Table 3-continued

Shoot treatment test/powdery mildew of cereal/protective

| Active compounds | | Active compound concentration in the spray liquor in % by weight | Infection in % of the untreated control |
|---|---|---|---|
| Cl–⟨⟩–⟨⟩–O–CH(triazole)–CH(O–CO–CH₃)–C(CH₃)₃ | (34) | 0.0005 | 25.0 |
| (2,4-Cl₂-C₆H₃)–O–CH(imidazole)–CH(O–CO–CH₃)–C(CH₃)₃ | (45) | 0.0005 | 58.8 |
| Br–⟨⟩–O–CH(triazole)–CH(O–CO–CH₃)–C(CH₃)₃ | (39) | 0.001 | 25.0 |
| (2,4-Cl₂-C₆H₃)–O–CH(triazole)–CH(O–CO–NH–C₆H₄–Cl)–C(CH₃)₃ | (2) | 0.001 | 6.3 |

EXAMPLE 4

Shoot treatment test/powdery mildew of cereals/curative (leaf-destructive mycosis)

To produce a suitable preparation of active compound, 0.25 part by weight of active compound was taken up in 25 parts by weight of dimethylformamide and 0.06 part by weight of alkylaryl polyglycol ether emulsifier and then 975 parts by weight of water were added. The concentrate was diluted with water to the desired final concentration of the spray liquor.

To test for curative activity the procedure followed was analogous, but in the converse sequence, to that for testing for protective activity in Example 3. The treatment of the single-leaved young barley plants with the preparation of active compound was carried out 48 hours after the inoculation, when the infection was already manifest.

After 6 days' dwell time of the plants at a temperature of 21°-22° C. and 80-90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The active compound was the more active, the lower was the degree of mildew infection.

The active compounds, active compound concentrations in the spray liquor and degrees of infection can be seen from the table which follows:

Table 4

Shoot treatment test/powdery mildew of cereals/curative

| Active compounds | | Active compound concentration in the spray liquor in % by weight | Infection in % of the untreated control |
|---|---|---|---|
| untreated | | — | 100.0 |
| (CH₃)₃C–⟨⟩–O–CH(triazole)–CH(OH)–C(CH₃)₃ (known) | (B) | 0.0025 | 25.0 |
| (2,4-Cl₂-C₆H₃)–O–CH(triazole)–CH(O–CO–CH₃)–C(CH₃)₃ | (5) | 0.0025 | 0.0 |

Table 4-continued

| | Shoot treatment test/powdery mildew of cereals/curative | | |
|---|---|---|---|
| Active compounds | | Active compound concentration in the spray liquor in % by weight | Infection in % of the untreated control |
| 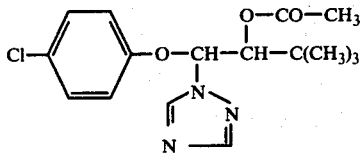 | (1) | 0.0025 | 0.0 |

EXAMPLE 5

Powdery mildew of barley test (Erysiphe graminis var. Hordei)/systemic (fungal disease of cereal shoots)

The active compounds were used as pulverulent seed treatment agents. They were prepared by extending the particular active compound with a mixture of equal parts by weight ot talc and kieselguhr to give a finely pulverulent mixture of the desired concentration of active compound.

For the treatment of seed, barley seed was shaken with the mixture of active compound and extender in a closed glass bottle. The seed was sown at the rate of 3 × 12 grains in flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had developed their first leaf, they were dusted with fresh spores of *Erysiphe graminis var. Hordei* and grown further at <°-22° C. and 80–90% relative atmospheric humidity and 16 hours' exposure to light. The typical mildew pustules formed on the leaves over the course of 6 days.

The degree of infestion was expressed as a percentage of the infection of the untreated control plants. Thus, 0% denotes no infection and 100% denoted the same degree of infection as in the case of the untreated control. The more active the compound, the lower was the degree of mildew infection.

The active compounds and concentrations of active compound in the seed treatment agent, as well as the amount used of the latter, and the percentage infection with mildew can be seen from the table which follows:

Table 5

| | Powdery mildew of barley test (*Erysiphe gramis var. hordei*)/systemic | | | |
|---|---|---|---|---|
| Active compounds | | Active compound concentration in the dressing in % by weight | Amount of dressing in g/kg of seed | Infection in % of the untreated control |
| without dressing | | — | — | 100.0 |
| 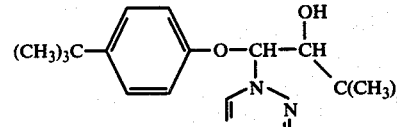 (known) | (D) | 25 | 10 | 100.0 |
| 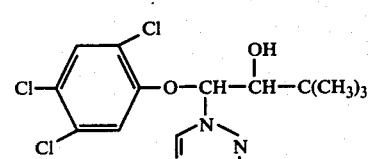 (known) | (B) | 25 | 10 | 66.3 |
| 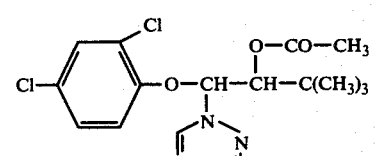 | (5) | 25 | 10 | 0.0 |
| 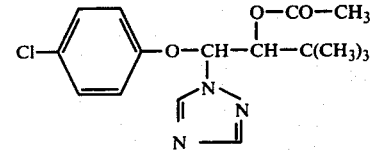 | (1) | 25 | 10 | 0.0 |

Table 5-continued

Powdery mildew of barley test (*Erysiphe gramis var. hordei*)/systemic

| Active compounds | | Active compound concentration in the dressing in % by weight | Amount of dressing in g/kg of seed | Infection in % of the untreated control |
|---|---|---|---|---|
| [structure with 4-Cl-phenyl, O-CO-CH₂-O-phenyl, C(CH₃)₃, triazole] | (26) | 2.5 | 2 | 33.8 |
| [structure with 4-Cl-phenyl, O-CO-CH₂-CH₃, C(CH₃)₃, triazole] | (27) | 2.5 | 2 | 0.0 |
| [structure with 4-Cl-phenyl, O-CO-CH₂Cl, C(CH₃)₃, triazole] | (28) | 2.5 | 2 | 0.0 |
| Cu[structure with 3-Cl-phenyl, O-CO-CH₃, C(CH₃)₃, triazole]₂ Cl₂ | (4) | 2.5 | 2 | 0.0 |
| [structure with 4-I-phenyl, O-CO-CH₃, C(CH₃)₃, triazole] | (29) | 2.5 | 2 | 0.0 |
| [structure with 2-Cl-phenyl, O-CO-CH₃, C(CH₃)₃, triazole] | (30) | 2.5 | 2 | 25.0 |
| [structure with 4-Br-phenyl, O-CO-CH₃, C(CH₃)₃, triazole] | (39) | 5 | 2 | 0.0 |
| [structure with 2-CH₃-4-Cl-phenyl, O-CO-CH₃, C(CH₃)₃, triazole] | (32) | 5 | 2 | 0.0 |

Table 5-continued

| Powdery mildew of barley test (*Erysiphe gramis var. hordei*)/systemic | | | |
|---|---|---|---|
| Active compounds | Active compound concentration in the dressing in % by weight | Amount of dressing in g/kg of seed | Infection in % of the untreated control |
| (40) [2,4-dichlorophenoxy-CH(triazolyl)-CH(OCOCH₃)-C(CH₃)₃] | 2.5 | 2 | 0.0 |
| (41) [4-fluorophenoxy-CH(triazolyl)-CH(OCOCH₃)-C(CH₃)₃] | 2.5 | 2 | 0.0 |
| (2) [2,4-dichlorophenoxy-CH(triazolyl)-CH(O-CO-NH-4-chlorophenyl)-C(CH₃)₃] | 25 | 10 | 0.0 |

EXAMPLE 6

Shoot treatment test/cereal rust/protective (leaf-destructive mycosis)

To produce a suitable preparation of active compound, 0.25 part by weight of active compound was taken up in 25 parts by weight of dimethylforamide and 0.06 part by weight of alkylaryl polyglycol ether emulsifier and then 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20° C. and 100% relative atmospheric humidity.

After 10 days' dwell time of the plants at a temperature of 20° C. and 80–90% atmospheric humidity, the occurrence of rust pustules on the plants was evaluated. The degree of infection was expressed as a percentage of the infection of the untreated control plants. 0% denoted no infection and 100% denoted the same degree of infection as in the case of the untreated control. The more active the compound, the lower was the degree of rust infection.

The active compounds, active compound concentrations in the spray liquor and degrees of infection can be seen from the table which follows:

Table 6

| Shoot treatment test/cereal rust/protective | | |
|---|---|---|
| Active compounds | Active compound concentration in the spray liquor in % by weight | Infection in % of the untreated control |
| untreated | — | 100.0 |
| (CH₃)₃C-phenyl-O-CH(triazolyl)-CH(OH)-C(CH₃)₃ (known) (D) | 0.025 | 75.0 |
| biphenyl-O-CH(triazolyl)-CH(OCOCH₃)-C(CH₃)₃ (6) | 0.025 | 0.0 |

Table 6-continued

Shoot treatment test/cereal rust/protective

| Active compounds | Active compound concentration in the spray liquor in % by weight | Infection in % of the untreated control |
|---|---|---|
| Compound (12): 4-Cl, 3-CH₃-phenoxy with O-CO-CH₃, C(CH₃)₃, triazole | 0.025 | 0.0 |
| Compound (18): biphenyl-O- with O-CO-NH-CH₃, C(CH₃)₃, triazole | 0.025 | 13.8 |
| Compound (40): 2,4,6-trichlorophenoxy with O-CO-CH₃, C(CH₃)₃, triazole | 0.01 | 8.8 |

EXAMPLE 7

Germinating capacity test/seed treatment/wheat

To prepare a suitable dry dressing; the active compound was diluted with a mixture of equal parts by weight of talc and kieselguhr to give a finely pulverulent mixture of the desired concentration of active compound.

For the dressing treatment, the wheat seed was shaken with the dressing in a closed glass bottle. The seed was sown at the rate of 2 × 100 grains in seed boxes on sterile quartz sand. 5 cm of sterile brick grit was used as the covering layer. The boxes were set up in a greenhouse at a temperature of +15° C. and were kept at a normal moisture.

The number of plants which had emerged on the 21st day characterised the germinating capacity of the seed under the influence of the preparations. If this value was markedly lower than that of the untreated control boxes, the germinating capacity had been impaired.

Table 7

Germinating capacity test/seed treatment/wheat

| Active compound | Amount of acitve compound used in mg/kg of seed | Number of emerged plants, in %, on the 21st day |
|---|---|---|
| without dressing | — | 83.0 |
| (F) 4-Cl-phenoxy with OH, C(CH₃)₃, triazole (known) | 500 | 32.5 |
| (G) 4-Br-phenoxy with OH, C(CH₃)₃, triazole (known) | 500 | 60.0 |
| (5) 2,4-diCl-phenoxy with O-CO-CH₃, C(CH₃)₃, triazole | 500 | 82.0 |
| (1) 4-Cl-phenoxy with O-CO-CH₃, C(CH₃)₃, triazole | 500 | 72.0 |

EXAMPLE 8

Phytotoxicity test/cucumbers

Solvent: 4.7 parts by weight of acetone
Emulsifier: 0.3 part by weight of alkylaryl polyglycol ether
Water: 95.0 parts by weight The amount of active compound required for the desired active compound concentration in the spray liquor was mixed with the stated amount of the solvent and the concentrate was diluted with the stated amount of water, which contained the stated additives. Young cucumber plants were sprayed with the spray liquor until dripping wet. After they had dried, the plants were set up in a greenhouse at a temperature of +20° C. and about 70% relative atmospheric humidity.

The plants were repeatedly evaluated with regard to damage. The evaluation was carried out on a 1-9 rating scheme. 1 denoted no damage and 9 denoted that the plant had been totally damaged or had died. The period of observation was, as a rule, 10 days.

The active compounds, active compound concentrations and results can be seen from the table which follows:

Table 8

Phytotoxicity test

| Active compound | Damage at an active compound concentration of 0.2% |
|---|---|
| Cl—⟨C₆H₄⟩—O—CH(N-triazolyl)—CH(OH)—C(CH₃)₃ (known) (F) | 5 |
| 2,4-Cl₂—⟨C₆H₃⟩—O—CH(N-triazolyl)—CH(OH)—C(CH₃)₃ (known) (G) | 5 |
| Br—⟨C₆H₄⟩—O—CH(N-triazolyl)—CH(OH)—C(CH₃)₃ (known) (C) | 5 |
| 2,4-Cl₂—⟨C₆H₃⟩—O—CH(N-triazolyl)—CH(O—CO—CH₃)—C(CH₃)₃ (5) | 2 |
| Cl—⟨C₆H₄⟩—O—CH(N-triazolyl)—CH(O—CO—CH₃)—C(CH₃)₃ (1) | 2 |
| 2,4-Cl₂—⟨C₆H₃⟩—O—CH(N-triazolyl)—CH(O—CO—CH₂—CH(CH₃)₂)—C(CH₃)₃ (36) | 3 |

Table 8-continued
Phytotoxicity test

| Active compound | Damage at an active compound concentration of 0.2% |
|---|---|
| (31) $O_2N$-C$_6H_4$-O-CH(N-triazole)-CH(O-CO-CH$_3$)-C(CH$_3$)$_3$ | 3 |
| (34) Cl-C$_6H_4$-C$_6H_4$-O-CH(N-triazole)-CH(O-CO-CH$_3$)-C(CH$_3$)$_3$ | 3 |
| (2) 2,4-Cl$_2$-C$_6H_3$-O-CH(N-triazole)-CH(O-CO-NH-C$_6H_4$-4-Cl)-C(CH$_3$)$_3$ | 3 |
| (6) C$_6H_5$-C$_6H_4$-O-CH(N-triazole)-CH(O-CO-CH$_3$)-C(CH$_3$)$_3$ | 4 |
| (9) 2-C$_6H_5$-C$_6H_4$-O-CH(N-triazole)-CH(O-CO-CH$_3$)-C(CH$_3$)$_3$ | 3 |
| (9a) [Cu{2-C$_6H_5$-C$_6H_4$-O-CH(N-triazole)-CH(O-CO-CH$_3$)-C(CH$_3$)$_3$}$_2$]Cl$_2$ | 3 |

Table 8-continued

| Phytotoxicity test | |
|---|---|
| Active compound | Damage at an active compound concentration of 0.2% |
| 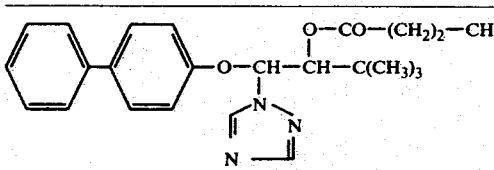 (10) | 3 |
| 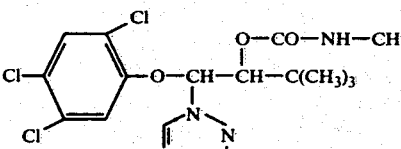 (19) | 3 |

EXAMPLE 9

Phytophthora test (tomatoes)/protective

Solvent: 4.7 parts by weight of acetone
Emulsifier: 0.3 part by weight of alkylaryl polyglycol ether
Water: 95.0 parts by weight The amount of the active compound required for the desired concentration of the active compound in the spray liquid was mixed with the stated amount of solvent and the concentrate was diluted with the stated amount of water which contained the stated addtitions.

Young tomato plants with 2 to 4 foliage leaves were sprayed with the spray liquid until dripping wet. The plants remained in a greenhouse for 24 hours at 20° C. and at a relative atmospheric humidity of 70%. The tomato plants were then inoculated with an aqueous spore suspension of Phytophthora infestans. The plants were brought into a moist chamber with an atmospheric humidity of 100% and a temperature of 18°-20° C.

After 5 days the infection of the tomato plants was determined. The assessment data were converted to percent infection: 0% means no infection; 100% means that the plants were totally infected.

The active compound, the concentration of the active compound and the results can be seen from the following table:

Table 9

| | Phytophthora test (tomatoes)/protective |
|---|---|
| Active compound | Infection in % at an active compound concentration (by weight) of 0.0025 % |
| 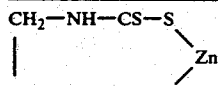 (known) (J) | 63 |
| 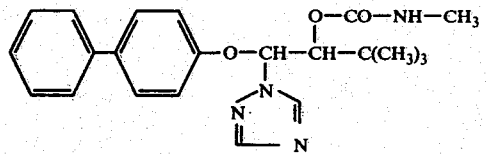 (18) | 6 |

EXAMPLE 10

Phytophthora test (tomatoes)/curative

Solvent: 4.7 parts by weight of acetone
Emulsifier: 0.3 part by weight of alkylaryl polyglycol ether
Water: 95.0 parts by weight The amount of the active compound required for the desired concentration of the active compound in the spray liquid was mixed with the stated amount of solvent and the concentrate was diluted with the stated amount of water which contained the stated additions.

Young tomato plants with 2 to 4 foliage leaves were inoculated with an aqueous spore suspension of Phytophthora infestans. The plants remain for 7 hours at 20° C. and at a relative atmospheric humidity of 100%.

After a short drying up time the plants were sprayed with the spray liquor, which had been prepared in the manner stated above, until they were dripping wet. The plants were then brought into a moist chamber with an atomospheric humidity of 100% and a temperature of 18°–20° C.

After 5 days the infection of the tomato plants was determined. The assessment data were converted to percent infection: 0% means no infection; 100% means that the plants were totally infected.

The active compound, the concentration of the active compound and the results can be seen from the following table:

Table 10
Phytophthora test (tomatoes)/curative

| Active compound | Infection in % at an active compound concentration of 0.025 % |
|---|---|
| 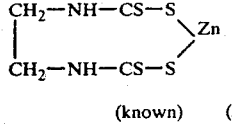 (known) (J) | 70 |
| 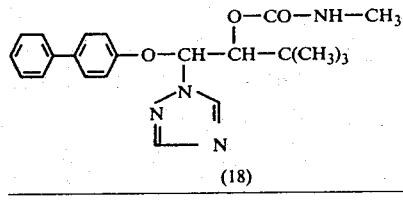 (18) | 17 |

The process of the present invention is illustrated by the following preparative examples.

EXAMPLE 11

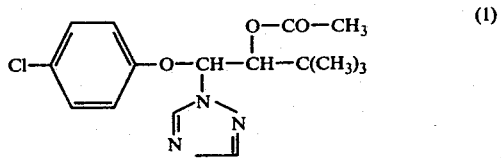 (1)

(a) Preparation of the starting material

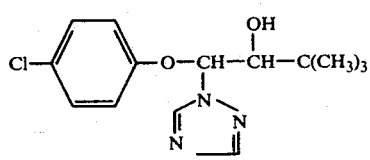

587 g (2 moles) of 1-(4-chlorophenoxy)-1-[1,2,4-triazolyl-(1)]-3,3-dimethyl-butan-2-one were dissolved in 3 l of methanol. A total of 80 g (2 moles) of sodium borohydride was added in portions of 5 g at 0° to 10° C., while stirring and cooling with ice, and the mixture was stirred for 2 hours at 5° to 10° C. and then for 12 hours at room temperature. It was then cooled to 10° C. and 300 g (3 moles) of concentrated aqueous hydrochloric acid were added at 10° to 20° C. After stirring for six hours at room temperature, the suspension obtained was diluted with 3.8 l of water which contained 400 g (4.8 moles) of sodium bicarbonate. The precipitate thereby produced was filtered off. 502 g (85% of theory) of 1-(4-chlorophenoxy)-[1,2,4-triazolyl-(1)]-3,3-dimethyl-butan-2-ol of melting point 112°–117° C. were obtained.

(b) Preparation in accordance with process variant (a)

8.0 g (0.1 mole) of acetyl chloride were added, at room temperature, to 29.5 g (0.1 mole) of 1-(4-chlorophenoxy)-1-[1,2,4-triazolyl-(1)]-3,3-dimethyl-butan-2-ol in 100 ml of ethyl acetate. The mixture was then heated for 4 hours under reflux, allowed to cool and concentrated by distilling off the solvent in vacuo. The residue was taken up in benzene and the solution was washed with aqueous sodium bicarbonate solution and dried over sodium sulfate. The solvent was distilled off in a waterpump vacuum and the residue was recrystallized from n-hexane. 15 g (44.5% of theory) of 2-acetoxy-1-(4-chlorophenoxy)-1-[1,2,4-triazolyl-(1)]-3,3-dimethyl-butane were obtained as an isomer mixture of melting point 86°–93° C.

A pure stereoisomer of melting point 153°–154° C. could be isolated by recrystallization from ethyl acetate.

(c) Preparation in accordance with process variant (b)

591 g (2 moles) of 1-(4-chlorophenoxy)-1-[1,2,4-triazolyl-(1)]-3,3-dimethyl-butan-2-ol in 1.2 l of acetic anhydride were heated with 10 g of sodium acetate for 16 hours at 100° C. The solution was then cooled and stirred into 5 l of ice water, while keeping the temperature at 20° to 25° C. A smeary, crystalline mass precipitated, which was taken up in 2.5 l of methylene chloride. The solution was washed with water and sodium bicarbonate solution, dried over sodium sulfate and concentrated in vacuo by distilling off the solvent. 674 g (100% of theory) of 2-acetoxy-1-(4-chlorophenoxy)-1-[1,2,4-triazolyl-(1)]-3,3-dimethyl-butane were obtained as an isomer mixture of melting point 88°–95° C.

On recrystallization from 500 ml of ethyl acetate, a pure stereoisomer of melting point 149°–153° C. could be isolated.

EXAMPLE 12

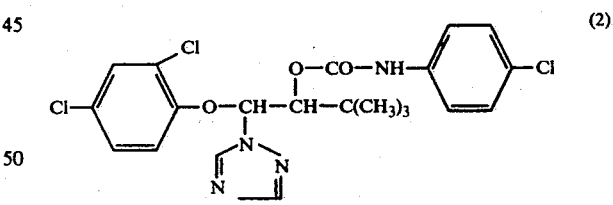 (2)

Preparation in accordance with process variant (c)

A solution of 3.1 g (0.02 mole) of 4-chlorophenylisocyanate in 50 ml of ether and 3 drops of triethylamine was added to 6.6 g (0.02 mole) of 1-(2,4-dichlorophenoxy)-1-[1,2,4-triazolyl-(1)]-3,3-dimethyl-butan-2-ol in 30 ml of ethyl acetate and 50 ml of absolute ether. The mixture was left to stand for 48 hours at room temperature, the solvents were distilled off in vacuo and the residue was recrystallized from petroleum ether/ether (1:1). 4.8 g (50% of theory) of 2-(4-chlorophenylcarbamoyl)-1-(2,4-dichlorophenoxy)-1-[1,2,4-triazolyl-(1)]-3,3-dimethylbutane were obtained as an isomer mixture of melting point 183°–184° C.

EXAMPLE 13

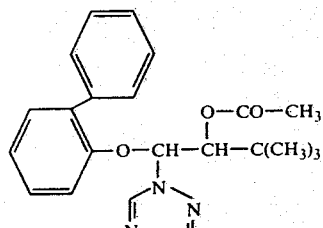

(3)

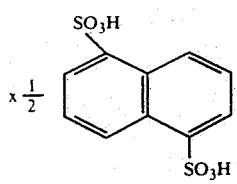

Salt formation 4.9 g (0.014 mole) of 1-(2-phenylphenoxy)-1-[1,2,4-triazolyl-(1)]-3,3-dimethyl-butan-2-ol in 30 ml of acetic anhydride were heated with 0.1 g of sodium acetate for 15 hours at 100° C. Thereafter, the mixture was allowed to cool and was stirred into 300 ml of water and extracted by shaking with 200 ml of chloroform. The chloroform solution was washed with four times 50 ml of water and once with 100 ml of saturated sodium bicarbonate solution, dried over sodium sulfate and concentrated by distilling off the solvent in vacuo. 50 ml of acetone, in which 1.44 g of naphthalene-1,5-disulfonic acid were dissolved, were added to the residue, whereupon the salt precipitated in a crystalline form. 3.1 g (42% of theory) of 2-acetoxy-1-(2-phenylphenoxy)-1-[1,2,4-triazolyl-(1)]-3,3-dimethyl-butane naphthalene-1,5-disulfonate were obtained as a stereoisomer of melting point 213° C.

EXAMPLE 14

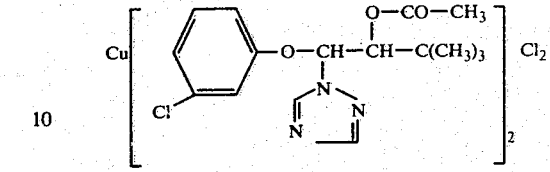

(4)

Complex formation 8.8 g (0.03 mole) of 1-(3-chlorophenoxy)-1-[1,2,4-triazolyl-(1)]-3,3-dimethyl-butan-2-ol in 45 ml of acetic anhydride were stirred with 0.1 g of sodium acetate for 15 hours at 100° C. When the solution had cooled it was added to 450 ml of water and the mixture was stirred for 15 hours at room temperature and extracted with three times 100 ml of methylene chloride. The combined organic phases were washed with 100 ml of water and 100 ml of saturated sodium bicarbonate solution, dried over sodium sulfate and concentrated by distilling off the solvent in vacuo. The residue was dissolved in 50 ml of ethanol. 2.4 g (0.014 mole) of copper dichloride in 7 ml of water were added. The mixture was concentrated in a waterpump vacuum, 100 ml of ethyl acetate were added to the residue and the crystalline precipitate formed was filtered off. 8.1 g (67% of theory) of bis-[2-acetoxy-1-(3-chlorophenoxy)-1-[1,2,4-triazolyl-(1)]-3,3-dimethyl-butane]-copper(II) chloride were obtained as an isomer mixture of melting point 181°–183° C.

The following compounds were obtained by methods analogous to those of the above examples.

Table 11

$$\text{(structure)} \quad O-CH-CH-C(CH_3)_3 \quad (I),$$
with O—CO—R and Az substituents

| Compound No. | $X_n$ | R | Position in which the 1,2,4-triazolyl radical Az is bonded | Melting point (° C) Isomer mixture | Melting point (° C) pure stereo-isomer |
|---|---|---|---|---|---|
| 5 | 2,4-Cl$_2$ | CH$_3$ | (1) | 55-96 | 154-56 |
| 6 | 4-phenyl | CH$_3$ | (1) | | 115-17 |
| 7 | 2,4,5-Cl$_3$ | CH$_3$ | (1) | | 116-18 |
| 8 | 2,5-Cl$_2$ | CH$_3$ | (1) | 135-41 | |
| 9 | 2-phenyl | CH$_3$ | (1) | | 162-64 |
| 9a | 2-phenyl | CH$_3$ | (1) | | 182 |
| 10 | 4-phenyl | n-C$_3$H$_7$ | (1) | | 82-84 |

Table 11-continued $$\underset{X_n}{\text{Ar}}-O-\underset{Az}{CH}-\underset{}{CH}-C(CH_3)_3 \quad (I),$$
(with O—CO—R on the middle CH)

| Compound No. | $X_n$ | R | Position in which the 1,2,4-triazol-yl radical Az is bonded | Melting point (° C) Isomer mixture | Melting point (° C) pure stereo-isomer |
|---|---|---|---|---|---|
| 11 | 4-phenyl | t-C$_4$H$_9$ | (1) | | 145 |
| 12 | 3-CH$_3$,4-Cl | CH$_3$ | (1) | | 133–36 |
| 13 | 2-CH$_3$,5-Cl | CH$_3$ | (1) | 109–13 | |
| 14 | 3,5-(CH$_3$)$_2$,4-Cl | CH$_3$ | (1) | | 144–46 |
| 15 | 3-NO$_2$,4-Cl | CH$_3$ | (1) | 166–72 | |
| 16 | 2-CH$_5$,5-NO$_2$ | CH$_3$ | (1) | | 117–19 |
| 17 | 4-phenyl | —NH—(4-Cl-phenyl) | (1) | | 194–96 |
| 18 | 4-phenyl | —NH—CH$_3$ | (1) | | 120–25 |
| 19 | 2,4,5-Cl$_3$ | —NH—CH$_3$ | (1) | | 182–84 |
| 20 | 2-phenyl | —NH—CH$_3$ | (1) | 170–75 | |
| 21 | 2,5-Cl$_2$ | —NH—CH$_3$ | (1) | 133–68 | |
| 22 | 3,4-(CH$_3$)$_2$ | (1) | | 180–89 | (xHCl) |
| 23 | 2-CH$_3$,5-Cl | ab,4 NH—CH$_3$ | (1) | | 163 |
| 24 | 3,5-(CH$_3$)$_2$, 4-Cl | —NH—CH$_3$ | (1) | 129–43 (xHCl) | |
| 25 | 3,4-(CH$_3$)$_2$ | CH$_3$ | (1) | | 182–84 (x½CuCl$_2$) |
| 26 | 4-Cl | —CH$_2$—O—phenyl | (1) | | 130–31 |
| 27 | 4-Cl | C$_2$H$_5$ | (1) | | 112–14 |
| 28 | 4-Cl | CH$_2$Cl | (1) | | 105–07 |
| 29 | 4-I | CH$_3$ | (1) | 90–96 | |
| 30 | 2-Cl | CH$_3$ | (1) | 102–08 | |
| 31 | 4-NO$_2$ | CH$_3$ | (1) | 131–35 | |
| 32 | 2-CH$_3$,4-Cl | CH$_3$ | (1) | 114–19 | |
| 33 | 2-Cl,4-phenyl | CH$_3$ | (1) | 113–24 | |
| 34 | 4-Cl-phenyl | (1) | 90–94 | | |
| 35 | 4-H-phenyl | CH$_3$ | (1) | | 103–08 |
| 36 | 2,4-Cl$_2$ | i-C$_4$H$_9$ | (1) | 93–95 | |
| 37 | 4-CH$_3$ | CH$_3$ | (1) | 92–101 | |
| 38 | 4-CH(O—CO—CH$_3$)-phenyl | CH$_3$ | (1) | | 200–04 (x½ 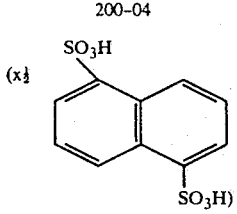) |
| 39 | 4-Br | CH$_3$ | (1) | 90–97 | |
| 40 | 2,4,6-Cl$_3$ | CH$_3$ | (1) | 125–31 | |

Table 11-continued

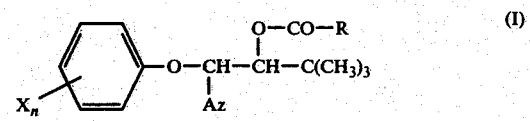

| Compound No. | $X_n$ | R | Position in which the 1,2,4-triazolyl radical Az is bonded | Melting point (°C) Isomer mixture | Melting point (°C) pure stereo-isomer |
|---|---|---|---|---|---|
| 41 | 4-F | CH₃ | (1) | 84–87 | |
| 42 | 3-Br | CH₃ | (1) | 79–83 | |
| 43 | 2-C₆H₅ | CH₃ | (4) | 123–33 | |
| 44 | 2-CH₃,5-Cl | —NH—CH₃ | (4) | 132–38 | |
| 45 | 2,4-Cl₂ | CH₃ | (4) | | 176–78 |
| 46 | 3,4-Cl₂ | —NH—CH₃ | (1) | 160–165 | |
| 47 | 4-CH₃ | (1) | 153–160 | | |
| 48 | 4-Cl,3-NO₂ | —NH—CH₃ | (1) | 180–200 | |
| 49 | 4-Br,2-Cl | CH₃ | (1) | 161 | |
| 50 | 4-Cl,3-CH₃ | —NH—CH₃ | (1) | 153–155 | |
| 51 | 4-Br,2-Cl | —NH—CH₃ | (1) | 128–130 | |
| 52 | 2,4-CH₃ | CH₃ | (1) | 102–122 | |
| 53 | 2,4-CH₃ | —NH—CH₃ | (1) | 124–129 | |
| 54 | 3-CF₃ | —NH—CH₃ | (1) | 100–104 | |
| 55 | 3-CF₃ | CH₃ | (1) | 105 | |
| 56 | 3,4-Cl₂ | CH₃ | (1) | 107–118 | |
| 57 | 4-Cl | —NH—CH₃ | (1) | | 142–144 |
| 58 | 4-Cl | —NH—C₂H₅ | (1) | | 114–118 |
| 59 | 4-Cl | —NH—CH(CH₃)₂ | (1) | 77–100 | |
| 60 | 4-Cl | —NH—C₃H₇-n | (1) | | 93–96 (form A) |
| 61 | 4-Cl | —NH—C₃H₇-n | (1) | | 154–156 (form B) |

Other compounds of the formula (I) which can be similarly prepared include:

Table 12

| $X_n$ | R | Position in which the 1,2,4-triazolyl radical Az is bonded |
|---|---|---|
| 4-NH₂ | —CH₂—CH=CH—CH₃ | (1) |
| 4-CN | —CH₂—C≡CH | (1) |
| 3-CF₃ | —C₂F₅ | (1) |
| 3-C₂H₅O—CO— | —C₆H₄—CN | (1) |
| 2-CH₃O— | —C₆H₄—Br | (1) |
| 4-C₂H₅S— | —C₆H₄—NO₂ | (1) |
| 4-Cl—C₆H₄—O— | —C₆H₄—NH₂ | (1) |
| 4-C₆H₄—CH(O-C₂H₅CO)— | —C₆H₄—C₂H₅ | (1) |
| — | —N(C₃H₇-n)₂ | (1) |
| — | —NH—C₆H₄—CN | (1) | and the like.

It will be appreciated that the instant specification and examples are set forth by way of illustration and not limitation, and that various modifications and changes may be made without departing from the spirit and scope of the present invention.

What is claimed is:

1. A 2-acyloxy-1-phenoxy-1-(1,2,4-triazolyl)-3,3-dimethyl-butane of the formula

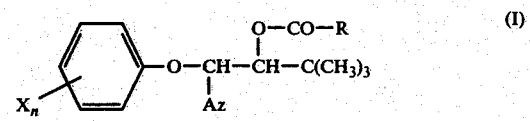

in which

R represents straight-chain or branched alkyl with 1 to 8 carbon atoms, straight-chain or branched alkenyl or alkynyl, each with 2 to 4 carbon atoms, halogenoalkyl with 1 to 2 carbon atoms and 1 to 5 halogen atoms, cycloalkyl with 5 to 7 carbon atoms, or optionally substituted phenyl or phenoxyalkyl which is optionally substituted in the phenyl part and has up to 2 carbon atoms in the alkyl part, in either case the substituents being selected from halogens, amino, cyano, nitro and alkyl with 1 or 2 carbon atoms, or alkyl-amino or dialkyl-amino with 1 to 4 carbon atoms in each alkyl part, or phenylamino which may optionally be substituted by halogen, nitro or cyano;

X represents halogen, amino, cyano, nitro, straight-chain or branched alkyl with up to 4 carbon atoms, cycloalkyl with 5 to 7 carbon atoms, halogenoalkyl with up to 2 carbon atoms and up to 5 halogen atoms, alkoxy-carbonyl with a total of up to 5 carbon atoms, alkoxy or alkylthio each with up to 2 carbon atoms, phenyl or phenoxy, either of which may optionally carry one or more substituents selected from halogens, amino, cyano, nitro and alkyl with 1 to 2 carbon atoms, or phenylalkyl with 1 or 2 carbon atoms in the alkyl part, in which alkylcarbonyloxy with a total of up to 3 carbon atoms may be a substituent in the alkyl part and halogen, nitro or cyano may be a substituent in the phenyl part, n represents 0, 1, 2 or 3, and Az represents the 1,2,4-triazolyl-1 or the 1,2,4-triazolyl-4 radical, in the form of the free base, a salt with a physiologically tolerated acid or a complex with a metal salt.

2. A compound according to claim 1 wherein such compound is 2-acetoxy-1-(4-chlorophenoxy)-1-[1,2,4-triazolyl-(1)]-3,3-dimethyl-butane of the formula

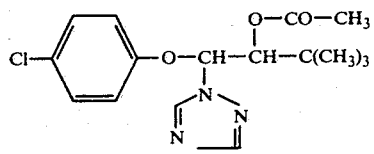

3. The compound according to claim 1 wherein such compound is 2-acetoxy-1-(2,4-dichlorophenoxy)-1-[1,2,4-triazolyl-(1)]-3,3-dimethyl-butane of the formula

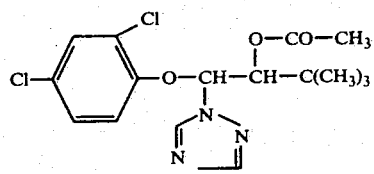

4. The compound according to claim 1 wherein such compound is 2-acetoxy-1-(4-diphenoxy)-1-[1,2,4-triazolyl-(1)]-3,3-dimethyl-butane of the formula

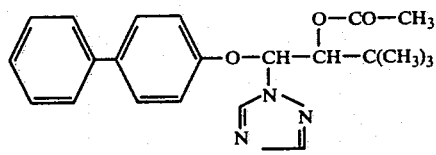

5. The compound according to claim 1 wherein such compound is 2-methylcarbamoyloxy-1-(4-diphenoxy)-1-[1,2,4-triazolyl-(1)]-3,3-dimethyl-butane of the formula

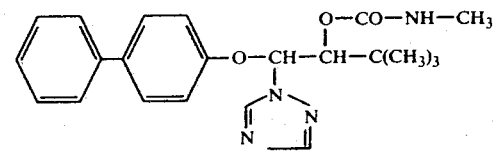

6. A compound according to claim 1 wherein such compound is 2-acetoxy-1-(4-bromophenoxy)-1-[1,2,4-triazolyl-(1)]-3,3-dimethyl-butane of the formula

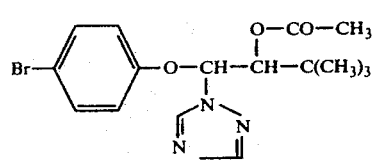

7. A fungicidal composition containing as active ingredient a fungicidally effective amount of a compound according to claim 1 in admixture with a diluent.

8. A method of combating fungi which comprises applying to the fungi, or to a habitat thereof, a fungicidally effective amount of a compound according to claim 1.

9. The method according to claim 8 in which said compound is:

2-acetoxy-1-(4-chlorophenoxy)-1-[1,2,4-triazolyl-(1)]-3,3-dimethyl-butane;

2-acetoxy-1-(2,4-dichlorophenoxy)-1-[1,2,4-triazolyl-(1)]-3,3-dimethyl-butane;

2-acetoxy-1-(4-diphenoxy)-1-[1,2,4-triazolyl-(1)]-3,3-dimethyl-butane;

2-methylcarbamoyloxy-1-(4-diphenoxy)-1-[1,2,4-triazolyl-(1)]-3,3-dimethyl-butane; or 2-acetoxy-1-(4-bromophenoxy)-1-[1,2,4-triazolyl(1)]-3,3-dimethyl-butane.

* * * * *